United States Patent [19]
Malette et al.

[11] 4,394,373
[45] Jul. 19, 1983

[54] METHOD OF ACHIEVING HEMOSTASIS

[76] Inventors: William G. Malette, 667 Parkwood La., Omaha, Nebr. 68132; Herbert J. Quigley, Jr., 9511 Mockingbird Dr., Omaha, Nebr. 68127

[21] Appl. No.: 251,321

[22] Filed: Apr. 6, 1981

[51] Int. Cl.$^3$ .................. A61K 31/60; A61K 35/56
[52] U.S. Cl. .................................... 424/95; 424/180
[58] Field of Search .................. 424/95, 180; 536/20

[56] References Cited
U.S. PATENT DOCUMENTS

| | | | |
|---|---|---|---|
| 3,903,268 | 9/1975 | Balassa | 424/95 |
| 3,911,116 | 10/1975 | Balassa | 424/95 |
| 3,914,414 | 10/1975 | Balassa | 424/95 |

OTHER PUBLICATIONS

The Merck Index, 9th Ed., Pub. by Merck & Co. Inc., N.J., 1976, p. 259.

Primary Examiner—Sam Rosen
Attorney, Agent, or Firm—Zarley, McKee, Thomte, Voorhees & Sease

[57] ABSTRACT

The method of achieving hemostasis in wounds, vascular grafts, vascular patches, cardiac valves and the like is described. Hemostasis is achieved in open wounds by topically administering chitosan, in liquid or powder form, to the wound. Hemostasis is achieved in vascular grafts, vascular patches, cardiac valves and areas to be sutured by either topically administering chitosan to the grafts, patches, valves and sutures or incorporating chitosan in the material of the grafts, patches, valves and sutures.

14 Claims, No Drawings

METHOD OF ACHIEVING HEMOSTASIS

BACKGROUND OF THE INVENTION

The U. S. Government has a nonexclusive, irrevocable, royalty-free license in this invention with power to grant licenses for all governmental purposes.

Medicine has long sought for a surface hemostatic agent which will act independently of normal clotting mechanisms. Present hemostatic agents such as gelatin sponges and purified blood proteins depend upon the natural clotting mechanisms for hemostasis. Patients who require anticoagulation for hypercoagulability and who are in danger of embolus are at high risk. Patients undergoing open heart operations must be anticoagulated during the period that they are dependent upon the pump oxgenator which leads to extensive blood loss during the procedure and during the immediate recovery period. Patients with hemophilia must be given highly expensive blood fractions during the surgical period.

Chitosan is a collective term applied to deacetylated chitins in various stages of deacetylation and depolymerization. Chitin is the structural polymer of the exoskeleton of arthropods and cell walls of fungi. It is composed of poly-N-Acetyl glucosamine units. These are linked by Beta 1-4 glycosidic bonds into a linear polymer containing 2,000 to 3,000 units. U.S. Pat. No. 3,533,940 describes the technology for the preparation of chitosan.

Chitosan is a derivative of solid waste from shell fish processing and can be extracted from fungus culture. Chitin is generally isolated and purified by first dissolving away the inorganic material, calcium carbonate, by treatment with hdyrochloric acid. After the protein material is removed by digestion with hot diluted alkali, the chitin is bleached with permanganate followed by treatment with oxalic acid. Partial deacetylization of chitin by treatment with concentrated alkali solution at 130 to 150 degrees centigrade yields products which are soluable in dilute acetic acid.

A common method to convert crab shell is as follows: The calcium carbonate is removed by immersing the shell in cold dilute hydrochloric acid, two to three hours are allowed for the reaction. The shell is then thoroughly rinsed with water. Protein is removed by treating the shell with caustic soda (3% strength). The shell is cooked in a 3% sodium hydroxide solution for a period of two hours at a temperature of 100° C. and at atmospheric pressure. The remains are rinsed thoroughly with water to remove all traces of sodium hydroxide and protein. The material is then bleached with potassium permanganate solution and rinsed with water. The material is then treated with oxalic acid to remove the permanganate solution. The material is then treated with a 40% caustic soda solution at 150° C. to partially deacetylate the chitin. This results in the formation of chitosan. By varying the amount of deacetylation, various viscosities of chitosan can be produced. The final pH of the chitosan solution is in the range of 4-5. It is possible to utilize chitosan in the following applications in various pH's and viscosities. However, the ideal mode is a solution of 2 gms. of chitosan per liter of acetic acid solution.

The prior art teaches that chitosan, when sulfated, acts as a weak anticoagulant in vitro and when given to animals. However, the experiments conducted by the inventors herein have found that chitosan (not sulfated) acts completely differently from that described in the prior art and that it does act as a fast and firm coagulating agent.

Therefore, it is a principal object of the invention to provide a method of achieving hemostasis in the absence of the normal clotting mechanisms.

A further object of the invention is to provide a method of achieving hemostasis in open wounds.

A further object of the invention is to provide a method of achieving hemostasis in vascular grafts, vascular patches, cardiac valves and areas to be sutured.

A still further object of the invention is to provide a method of achieving hemostasis through the use of chitosan.

These and other objects will be apparent to those skilled in the art.

SUMMARY OF THE INVENTION

Hemostasis is achieved in open wounds by placing chitosan, in liquid or powder form, in contact with the wound. Hemostasis in vascular grafts and vascular patches is achieved by either topically administering chitosan to the graft or patch or by incorporating chitosan in the material of the graft or patch. In areas to be sutured, hemostasis is achived by either topically administering chitosan to the suture or by incorporating the chitosan into the suture or by incorporating the chitosan in the material of the suture. Further, hemostasis is achieved in cardiac valve surgery by topically administering chitosan to the valve or by incorporating chitosan in the material of the valve.

DESCRIPTION OF THE PREFERRED METHOD

The inventors herein have discovered that chitosan, in liquid or powder form, does act as a fast and firm coagulating agent. The following experiments were conducted which supports the theory that chitosan is a coagulating agent.

EXAMPLE I

Normal human blood, without anticoagulation, was drawn and placed in several test tubes. Normal blood without chitosan was found to form a clot in ten minutes. One milliliter (ml.) aliquots of blood were placed in the test tubes with descending aliquots of chitosan placed herein. It was found that the blood having one milliliter of chitosan solution therein clotted in less than two minutes. Eight-tenths of a milliliter of chitosan solution in one milliliter of blood clotted in three and one-half minutes. Six-tenths of a milliliter of chitosan solution in one milliliter of blood clotted in four minutes.

EXAMPLE II

Five test tubes containing 1 ml. of heparinized blood were initially prepared. Chitosan solution was added to four of the test tubes in the amounts of 1 ml., 8/10ths of a ml., 6/10ths of a ml., and 4/10ths of a ml., respectively. One of the heparinized blood samples was not treated with chitosan so that the sample would act as a control sample. In the test tube containing 1 ml. of chitosan, the heparinized blood clotted in one minute and fifteen seconds. The 8/10ths of a ml. sample clotted in one minute and forty-five seconds. The 6/10ths and 4/10ths samples required more time to clot. The control tube containing the heparinized blood without chitosan did not clot. This experiment reveals that the normal clotting mechanism of the blood is not necessary for the coagulum produced by chitosan.

EXAMPLE III

Blood that has physically been defibrinated contains none of the clotting factors of normal blood. Blood, being defibrinated, eliminates all of the factors in normal blood clotting. One ml. of chitosan solution was added to 1 ml. of defibrinated blood and a firm blood clot was achieved in forty seconds. A control tube containing the same blood but without chitosan did not clot. This experiment reveals that neither fibrinogen nor any of the other clotting factors need be present in the coagulation reaction of chitosan in blood.

EXAMPLE IV

This experiment was conducted to determine whether serum proteins could in some way be involved in the clot formed by chitosan and blood. A 5% human serum albumin in aliquots was combined with a chitosan solution with no observable clot being formed.

EXAMPLE V

Human serum globulin (165 mg. per ml) was mixed with a chitosan solution with no resultant clot being formed. The results of Examples IV and V reveal that the coagulation observed with chitosan and blood is not dependent upon albumin or globulin.

EXAMPLE VI

Th cellular components of blood were washed four times in saline to remove the plasma and suspended in saline to their normal hematocrit. Washed red cells at a 40% hematocrit mixture was mixed one to one with chitosan. A firm clot was obtained in thirty seconds. This experiment indicates that the presence of cellular components in blood are active in forming the coagulum induced by chitosan.

Thus, the experiments or examples listed above indicate that chitosan may be employed to achieve hemostasis. Chitosan may be employed in medicine and surgery by either direct application of the viscous liquid chitosan, lyophilized powder of such a solution or dried, finely ground material. The dry forms of chitosan may be applied by insufflation, dusting or direct application. The chitosan may also be applied to such prostheses as vascular grafts, heart valves, vascular patches or other prostheses. When the chitosan material is applied to open wounds, as described above, hemostasis will be achieved. Further, the incorporation of or the application to vascular grafts, heart valves, vascular patches, etc. will enhance the hemostatic action.

Thus it can be seen that a novel method of achieving hemostasis through the use of chitosan has been described.

We claim:

1. The method of achieving hemostasis in bleeding open wounds which comprises placing chitosan in contact with the wound.

2. The method of claim 1 wherein the chitosan is topically administered to the wound.

3. The method of claim 1 wherein the chitosan is in liquid form.

4. The method of claim 2 wherein the chitosan is in powder form.

5. The method of achieving hemostasis in vascular grafts which comprises placing chitosan in contact with the bleeding graft area.

6. The method of claim 5 wherein the chitosan is topically administered to the graft area.

7. The method of claim 5 wherein the chitosan is incorporated in the material of the vascular graft.

8. The method of achieving hemostasis in vascular patches which comprises placing chitosan in contact with the bleeding vascular patch area.

9. The method of claim 8 wherein the chitosan is topically administered to the patch area.

10. The method of claim 8 wherein the chitosan is incorporated in the material of the vascular patch.

11. The method of achieving hemostasis in a bleeding sutured area which comprises incorporating chitosan in the suture material and applying it to the bleeding area.

12. The method of achieving hemostasis in a bleeding cardiac valve area which comprises placing chitosan in contact with the valve.

13. The method of claim 12 wherein the chitosan is incorporated in the material of the cardiac valve.

14. The method of achieving hemostasis which comprises placing chitosan in contact with the blood to be clotted.

* * * * *